(12) United States Patent
Faidi et al.

(10) Patent No.: US 8,418,560 B2
(45) Date of Patent: Apr. 16, 2013

(54) COMPOSITE FIBER WAVE INSPECTION SYSTEM AND METHOD

(75) Inventors: Waseem Ibrahim Faidi, Schenectady, NY (US); Del Charles Davenport, The Woodlands, TN (US); Chandra Sekher Yerramalli, Niskayuna, NY (US); Shu Ching Quek, Somerville, MA (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 13/192,747

(22) Filed: Jul. 28, 2011

(65) Prior Publication Data

US 2012/0033207 A1    Feb. 9, 2012

(51) Int. Cl.
  *G01N 9/24*    (2006.01)
(52) U.S. Cl.
  USPC .......................................... 73/606; 356/237.1
(58) Field of Classification Search ...................... 73/606
  See application file for complete search history.

(56) References Cited

U.S. PATENT DOCUMENTS

| 6,260,415 | B1 | 7/2001 | Goebel et al. |
| 6,393,384 | B1 | 5/2002 | Anthony et al. |
| 7,367,236 | B2 | 5/2008 | Georgeson et al. |
| 7,398,698 | B2 | 7/2008 | Griess et al. |
| 2010/0011865 | A1 | 1/2010 | Saxena et al. |
| 2010/0132137 | A1* | 6/2010 | Eggleston ...................... 15/21.1 |
| 2010/0218589 | A1* | 9/2010 | Dijkstra ........................ 73/1.82 |
| 2010/0329415 | A1* | 12/2010 | Stiesdal et al. .................... 378/4 |

OTHER PUBLICATIONS

Mouritz et al., "Non-Destructive Detection of Fatigue Damage in Thick Composites by Pulse-Echo Ultrasonics", Composites Science and Technology, vol. 60, Issue 1, pp. 23-32, Jan. 1, 2000.

* cited by examiner

*Primary Examiner* — Hezron E Williams
*Assistant Examiner* — Gregory J Redmann
(74) *Attorney, Agent, or Firm* — Ann M. Agosti

(57) ABSTRACT

A system for inspecting a wind turbine blade having a pair of shells surrounding a shear web. The system includes a scanning machine for taking images of an interior portion of the shells of the wind turbine blade, a measuring apparatus for taking numerous measurements of a defect imaged within the shells of the wind turbine blade, and a look-up table for ascertaining the theoretical strength of the wind turbine blade.

10 Claims, 4 Drawing Sheets

COMPOSITE FIBER WAVE INSPECTION SYSTEM AND METHOD

FIELD

The present disclosure relates to a system and method for inspecting layered objects, and more particularly to a system and method for inspecting for defects in turbine blades.

BACKGROUND

Wind turbine blades have a typical service life of about 20 years. During that time, wind turbine blades are subjected to a variety of forces, including static and dynamic lift and inertial and drag loads. Further, wind turbine blades must endure these forces over a wide range of environmental conditions, such as temperature extremes, ultraviolet light, precipitation (rain, snow, sleet, and hail), and bird strikes. Wind turbine blades must be specially constructed so that they withstand the myriad forces and conditions over their 20 year service life by combining low weight and low rotational inertia with high rigidity and resistance to fatigue and wear.

A typical wind turbine blade is constructed of layers of an outer skin supported by a primary spar. For example, and as illustrated in FIGS. 1-3, a wind turbine blade 100 has a turbine tip 102 and an opposing turbine root 104. Extending between the tip 102 and the root 104 are a spar cap 106 and a shear web 108. The shear web 108 serves as the main structural support within a turbine blade 100. The spar cap 106 is a glass portion running the length of the turbine blade coincident with the shear web 108 and it serves to take the tensile load of the blade 100.

Turbine blades, such as turbine blade 100, are formed in shells. For example, a first shell 105a extending from a leading edge 114 and a trailing edge 116 and including a suction surface 118 is positioned within a mold. This first shell 105a includes areas that include fiber-reinforced material 110 and other areas that include a core material 112. The core material portion may be composed of, for example, foam, balsa wood, or engineered core materials. Foam cores may include, for example, polyvinyl chloride (PVC), urethane, or polyethylene terephthalate (PET). Balsa wood has low cost, good shear properties, but a higher weight than the other core materials. Examples of engineered core materials include Webcore TYCOR® and NexCore™

The first shell 105a is placed in the mold such that the suction surface 118 is against the mold and a surface B is exposed. A second shell 105b extending from the leading edge 114 to the trailing edge 116 and including a pressure surface 120 is placed in a second mold such that the pressure surface 120 is against the mold and a surface B is exposed. As with the first shell 105a, the second shell 105b includes areas that are primarily glass and other areas that include the core material 112.

The shells 105a, 105b may be applied as multiple thin layers. Each of the layers may be a fiber-resin matrix. The layers of shells 105a, 105b may be formed of E-glass fiber or a carbon fiber bonded with a composite resin. Other potential composite materials include graphite, boron, aramid, such as KEVLAR®, and other organic materials and hybrid fiber mixes that can form reinforcing fibers. The reinforcing fibers may be in the form of a continuous strand mat (CSM), woven, or unidirectional mat (UNI). There are two main classes of polymer resin matrices—thermoset resins and thermoplastic resins. Thermoset resins include epoxy, phenols, bismaleimide, and polyimide, while thermoplastic resins include polyamide such as NYLON®, polysulfone, polyphenylene sulfide, and polyetheretherketone (PEEK). The matrix holds the fibers in place and, under an applied load, deforms and distributes stress to the fibers.

The composite layers may be formed into laminate or sandwich structures. Laminate structures include successive layers of composite materials bonded together. Sandwich structures include a low-density core between layers of composite materials.

The strengthening effect of the fiber reinforcements found in the layers of shells 150a, 105b depends on the percentage of fibers (also known as the fiber volume fraction), the types of fibers, the orientation of the fibers with respect to the direction of the loads, and the bond strength between the fibers and the matrix.

Sometimes, during construction of the molded shells 105a, 105b a defect can occur that reverberates throughout the multiple layers of either the first shell 105a or the second shell 105b or at the bond site between the spar cap 106 and the first shell 105a. The typical areas of concern for a defect are at the leading edge 114, the trailing edge 116, and near the spar cap 106. These three areas each carries the tensile loading of the blade 100, and so any bending of the fibers in a span-wise direction 124 in these sections reduces the strength of the fibers. For example, a burr or other anomaly may protrude from the B surface of the first shell 105a at the spar cap 106 or from the B surfaces of either shells 105a, 105b at the leading edge 114 or the trailing edge 116.

Depending upon where the anomaly is located in the first or second shells 105a, 105b, the anomaly may be visible in surfaces B while in the mold. Since surfaces B are interior surfaces of the blade 100 once it is constructed, any anomaly that may have been visible on either of surfaces B would no longer be visible after the first and second shells 105a, 105b are glued together to form the blade 100. Since the suction surface 118 and the pressure surface 120 are against the molds, these sides will not move and will contour the molds. Thus, any defect or wrinkle can only be detected from the B surfaces. The depth of the anomaly within the shells 105a, 105b determines whether the anomaly is visibly detectable on the B surfaces. So, if the anomaly is located nearer to a leading edge 114, sufficient layers of material within the first or second shells 105a, 105b may be applied over the anomaly to render the anomaly invisible to an external inspection of surface B prior to gluing. Conversely, if the anomaly is located nearer to a trailing edge 116, there may not be enough layers of material within the first or second shells 105a, 105b to render the anomaly invisible to an external inspection of surface B prior to gluing.

Anomalies in the construction of wind turbine blades, whether visible to external inspection prior to gluing or not, affect the strength of the turbine blade. Some anomalies create such an adverse effect on the strength of the turbine blade that the turbine blades are considered out of spec and do not pass inspection. In such instances, the turbine blades must either be sent back to be corrected or scrapped.

Current inspection techniques include an external inspection prior to gluing the two shells 105a, 105b together, coupled with a look-up table. A visual inspection of the shells prior to gluing may show an externally visible defect. Such an externally visible defect can be measured for its length (L) and its height ($a_e$). Current look-up tables include strength reductions for respective external defect aspects (L/$a_e$).

Current inspection techniques are all external and take place prior to gluing, and thus the only parameters of a defect that are measured are the external defect aspects of length (L) and height ($a_e$). Where the defect is located within a wind turbine blade affects the ultimate theoretical strength of the wind turbine blade, and current inspection techniques are not able to ascertain locations within a wind turbine blade. Additionally, if the defect is sited such that it is not visible from an external inspection of surfaces B prior to gluing, current inspection techniques will be unable to detect a defect, and thus may pass wind turbine blades that are strength compromised.

What is desired is an inspection technique that is capable of determining more parameters of a defect and is capable of determining a defect exists even though it is not externally visible.

SUMMARY

An embodiment provides a system for inspecting a layered object. The system includes a scanning machine for taking images of an interior portion of the layered object, a measuring apparatus for taking numerous measurements of a defect imaged within the layered object, and a look-up table for ascertaining the theoretical strength of the layered object.

An embodiment provides a method for inspecting a layered object. The method includes performing a scan of an interior portion of a layered object, taking measurements of internal parameters of a defect imaged within the layered object, and ascertaining the theoretical strength of the layered object based in part on the measurements of the internal and external characteristics These and other features, aspects and advantages of the present invention may be further understood and/or illustrated when the following detailed description is considered along with the attached drawings.

DETAILED DESCRIPTION

The present specification provides certain definitions and methods to better define the embodiments and aspects of the invention and to guide those of ordinary skill in the art in the practice of its fabrication. Provision, or lack of the provision, of a definition for a particular term or phrase is not meant to imply any particular importance, or lack thereof; rather, and unless otherwise noted, terms are to be understood according to conventional usage by those of ordinary skill in the relevant art.

Unless defined otherwise, technical and scientific terms used herein have the same meaning as is commonly understood by one of skill in the art to which this invention belongs. The terms "first", "second", and the like, as used herein do not denote any order, quantity, or importance, but rather are used to distinguish one element from another. Also, the terms "a" and "an" do not denote a limitation of quantity, but rather denote the presence of at least one of the referenced item, and the terms "front", "back", "bottom", and/or "top", unless otherwise noted, are merely used for convenience of description, and are not limited to any one position or spatial orientation. If ranges are disclosed, the endpoints of all ranges directed to the same component or property are inclusive and independently combinable (e.g., ranges of "up to about 25 wt. %, or, more specifically, about 5 wt. % to about 20 wt. %," is inclusive of the endpoints and all intermediate values of the ranges of "about 5 wt. % to about 25 wt. %," etc.).

The modifier "about" used in connection with a quantity is inclusive of the stated value and has the meaning dictated by the context (e.g., includes the degree of error associated with measurement of the particular quantity). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described inventive features may be combined in any suitable manner in the various embodiments.

Figure 1:
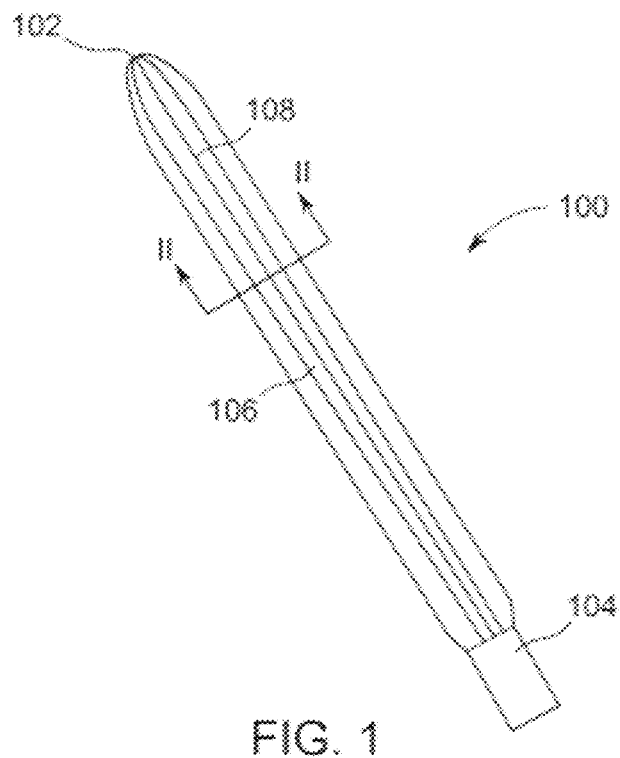
FIG. 1 is a schematic view of a wind turbine blade.
Figure 2:
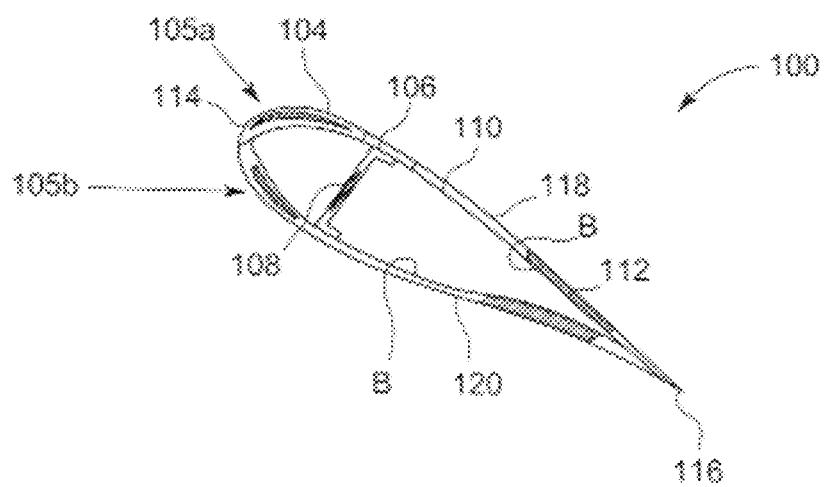
FIG. 2 is a partial schematic view of a wind turbine blade.
Figure 3:
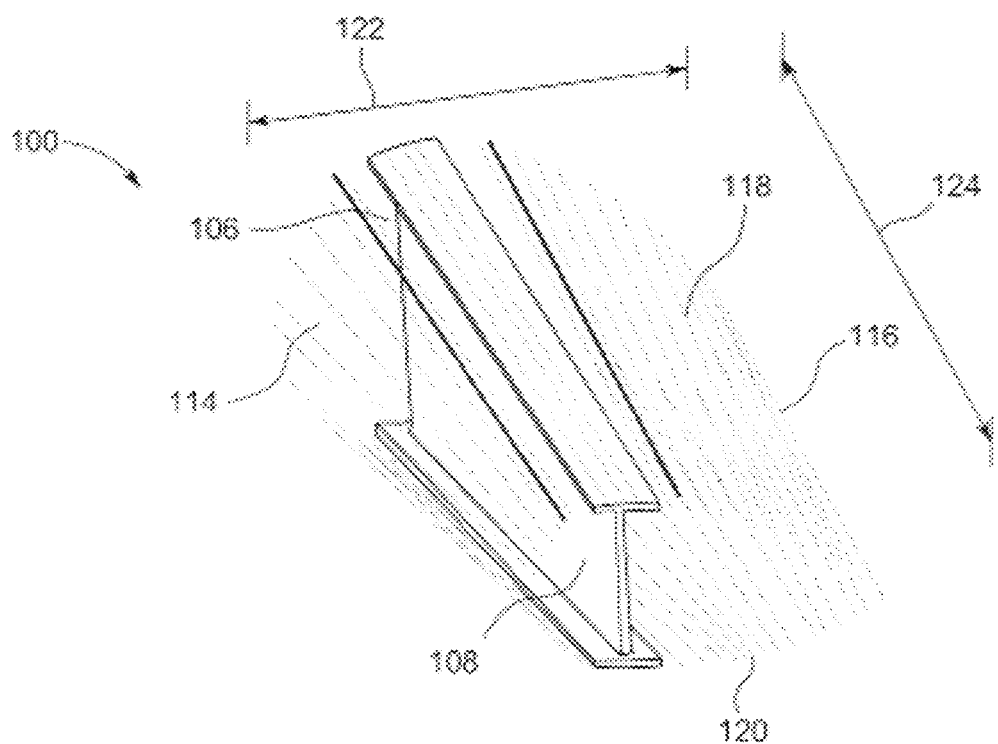
FIG. 3 is a schematic view of an internal shear web, a spar cap and a core material section of a wind turbine blade.

Layered objects, such as wind turbine blades illustrated in FIGS. 1-3, are formed through matrixed layers being successively applied over an internal skeleton. Sometimes, defects occur in the materials used to form wind turbine blades and other layered objects.

The wind turbine blade 100 schematically depicted in FIGS. 1-3 includes as a skeleton an internal shear web 108, a spar cap 106, and a core material section 112. Layers of material are applied over the skeleton of the wind turbine blade 100 to form the shells 105a, 105b. Some areas of the shells 150a, 105b have more matrixed layers than other areas. For example, there are more matrixed layers at the leading edge 114 of the wind turbine blade than are at the trailing edge 116.

The wind turbine blade 100 includes a suction surface 118 and an opposing pressure surface 120. The layers of material making up the two shells are applied in a chord-wise direction 122. The direction of the spar cap 106 and the shear web 108 is called the span-wise direction 124.

An embodiment of the invention includes subjecting layered objects, such as a wind turbine blade 100, to non-destructive imaging inspection to image an interior portion of the layered object. Examples of suitable non-destructive imaging include ultrasound imaging, including phased array probes capable of generating a cross-sectional image without mechanical scanning and a single element probe with a mechanical scanning mechanism. Further examples of suitable non-destructive imaging include x-ray computed tomography imaging, and laminographic imaging. Each of these non-destructive imaging techniques is capable of taking images of internal structures within a layered object. Further, each of these non-destructive imaging techniques is capable of taking multiple image slices through the layered object. For example, these non-destructive imaging techniques can take multiple image slices in either a chord-wise direction 122 or a span-wise direction 124.

Figure 4:
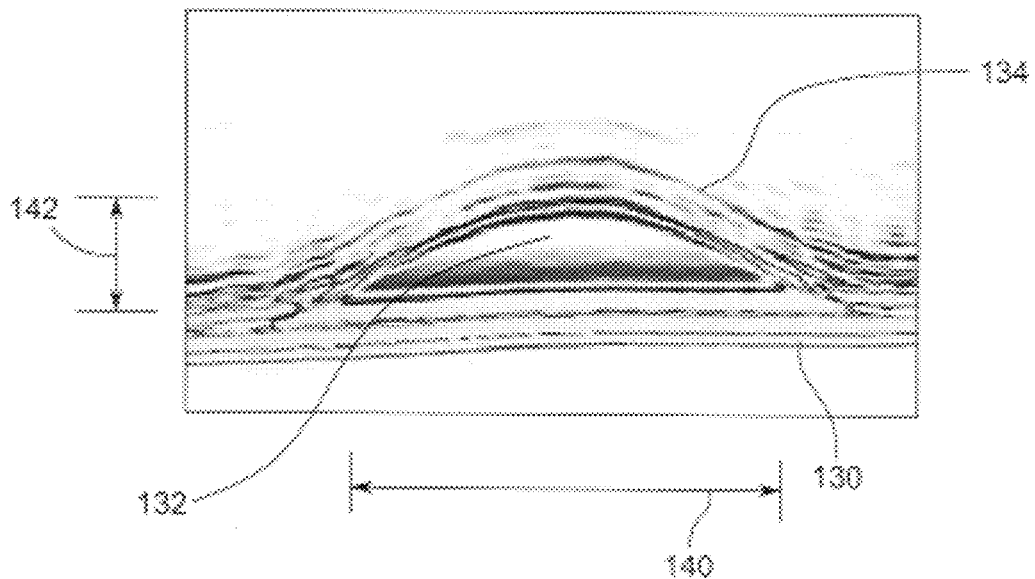
FIG. 4 is an ultrasound image of a defect within layers of a wind turbine blade.

FIG. 4 illustrates a portion of an image slice taken with an ultrasound machine. The ultrasound machine may include a plurality of phased array probes capable of generating a cross-sectional image without mechanical scanning or it may include a single element probe with a mechanical scanning mechanism. The image slice shows a plurality of shell layers 130 located at a lower extent in the image. Further, a defect 132 is shown above the layers 130. Finally, affected layers 134 are shown overlaying the defect 132. An internal length $L_o$ 140 of the defect 132 can be measured from the scanned image. Further, an internal height $a_i$ 142 of the defect 132 can be measured from the scanned image.

Figure 5:
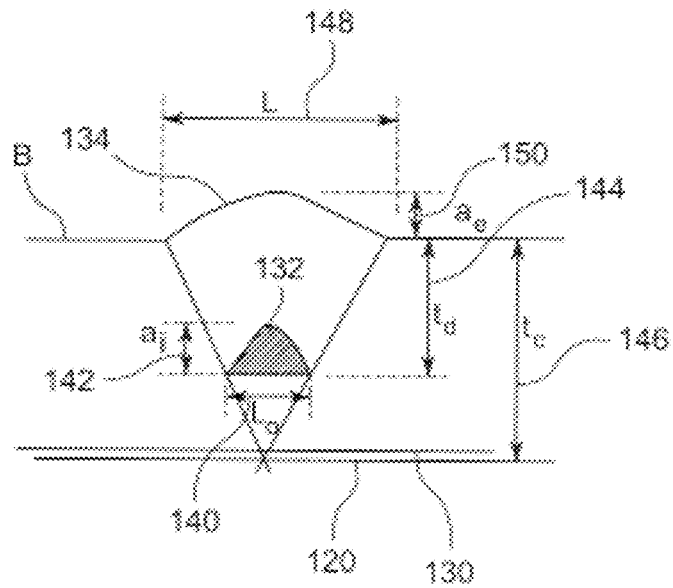
FIG. 5 is a schematic view of a defect within layers of a wind turbine blade.

FIG. 5 illustrates schematically a defect 132 located at a position between the surface B and the pressure surface 120 of a layered object, such as the wind turbine blade 100 (FIGS. 1-3). It should be appreciated that the defect 132 can be located in shell 105b as illustrated or in shell 105a and the surface opposing the surface B can be suction surface 118. Through non-destructive imaging, the defect 132 can be can be imaged and its length $L_o$ 140 and its height $a_i$ 142 can be ascertained. Further, either through manual or other visual inspection the external length L 148 and the external height $a_e$ 150 of the defect 132 can also be ascertained. For example, known visual inspection techniques include running a hand along surface B to detect an anomaly, using a flashlight to create a shadow effect from a bulge, or looking at an edge of the blade once the shell is decanted from the mold to look for a wave in the fiber plies. The external length L 148 and the external height $a_e$ 150 are essentially the extent to which the outer affected layers 134 remain affected by the defect 132.

Further measurements can also be made of other parameters of the defect 132. For example, measurements can be taken of the thickness $t_c$ 146 of the layered object at the location of the defect 132 as well as the depth $t_d$ 144 within the layered object at which the defect 132 occurs.

The ratio $t_d/t_c$ is an important ratio in considering the theoretical strength of a layered object, such as the wind turbine blade 100. Where a defect can be found within the layered object affects the ultimate strength such an object has. One reason for this is that layers above the defect, the affected layers 134, are bulged out of plane from unaffected layers 130 located beneath the defect. This bulging out of plane causes the individual layers to have a lessened individual strength, and the combined strength of the bulging out of plane layers is lessened as a group.

For example, suppose the ratio $t_d/t_c$ is 1, or said a different way, the defect 132 is located at the second surface 116, then a certain percentage of layers, namely 100%, may be affected by the defect 132. Instead, if the ratio $t_d/t_c$ is 0.5, or the defect 132 is located in the middle of the layered object, then only 50% of the layers may be affected by the defect 132. Thus, for a ratio $t_d/t_c$ of 0.5, the strength of the layered object will be greater than for a ratio $t_d/t_c$ of 1.

Another ratio of importance is the ratio of the internal height $a_i$ to the total thickness $t_c$ at which the defect 132 is found. It has been discovered that when the ratio $a_i/t_c$ increases toward 1, the strength of the layered object decreases.

Figure 6:
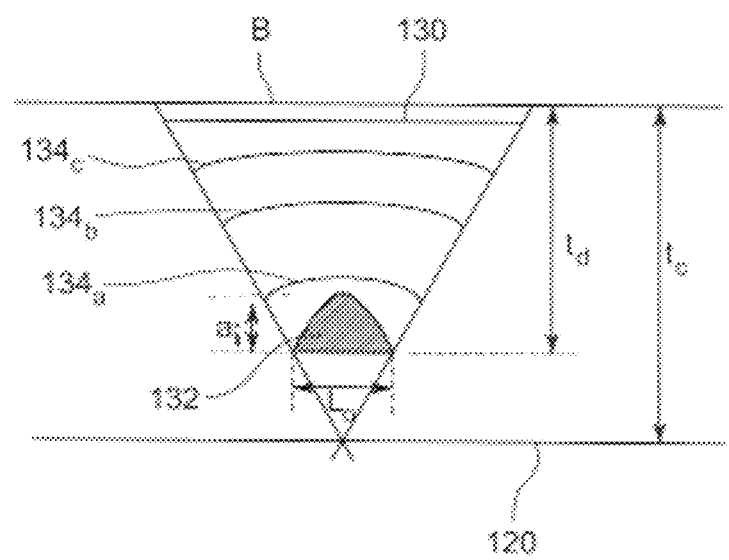
FIG. 6 is a schematic view of a defect, invisible from external detection, within layers of a wind turbine blade.

It should be appreciated that the defect 132 could be at such a depth, or located at such a place within the layered object that there are no externally visible signs of the defect 132. As illustrated in FIG. 6, a defect 132 is located between a first surface 114 and a second surface 116 of a layered object, such as a wind turbine blade 100. Affected layers are located between the defect 132 and the first surface 114. Specifically, affected layers $134_a$, $134_b$, and $134_c$ are shown located between the defect 132 and the first surface 114.

The amount to which the affected layers are affected diminishes as the distance from the defect 132 increases. Specifically, the height of the bulge of each affected layer decreases with increasing distance, while the length of the bulge of each affected layer increases with increasing distance. Thus, the height of the affected layer $134_a$ is greater than the height of the affected layer $134_b$, which in turn is greater than the height of the affected layer $134_c$. Eventually, the bulging is completely dissipated and unaffected layers 130 commence between the layer 134, and the first surface 114. Thus, the defect 132 is not visible externally and would go undetected using conventional inspection techniques. Using inspection techniques according to embodiments of the invention, however, such a defect 132 as illustrated in FIG. 5 would be detectable.

The measurements may be taken by either a single channel or multi-channel B-scan technique, which is a known scanning technique. Several equally spaced scans may be taken along the chord-wise axis 122 of the blade, along with a high resolution scan along the span-wise axis 124. This enables the chord-wise extent of the wave and the aspect ratio of the wave to be measured without additional scans.

Figure 7:
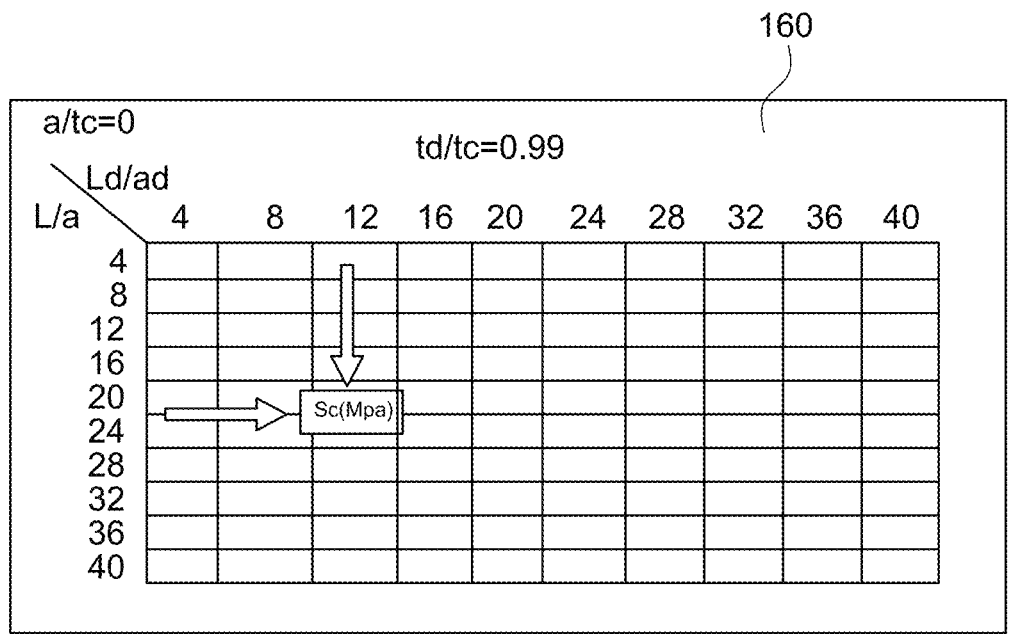
FIG. 7 is an exemplar of a look-up table for determining the mechanical strength of a wind turbine blade in accordance with an embodiment of the invention.

Once the measurements of the various parameters and aspects of the defect are taken, a look-up table 160 is utilized. The look-up table 160 of FIG. 7 provides strength profiles for, in addition to the external aspect ratio $L/a_e$, various internal parameters, including the internal aspect ratio $L_o/a_i$; the ratio of depth of the defect relative to the thickness of the layered object in the plane of the defect ($t_d/t_c$); and, the ratio of the height of the defect to the thickness of the layered object in the plane of the defect ($a_i/t_c$). The ratios are synchronized on the look-up table 160 by location on the blade 100 from the tip 102 to the root 104. Specifically, the ratios are synchronized in one meter increments from tip 102 to root 104 in the span-wise direction 124.

The non-destructive imaging system used for imaging the internal portions of the layered object takes multiple image slices throughout the layered object, taken at, for example, 10 millimeter spacing. There may be no defects imaged, one defect imaged, or multiple defects imaged. Obviously, for an instance when no defects are imaged, the structural strength of the layered object is not compromised and should pass inspection. For a single defect imaged, reference to the look-up table 160 based upon the measured parameters and aspects should guide one to determine the amount to which the structural strength of the layered object has been compromised. If compromised to too great an extent, the layered object can either be sent back to the manufacturing facility to be repaired or scrapped. For multiple defects, the look-up table 160 is referenced and the strength figures showing the greatest compromise of structural strength are used to determine whether the layered object passes inspection.

Figure 8:
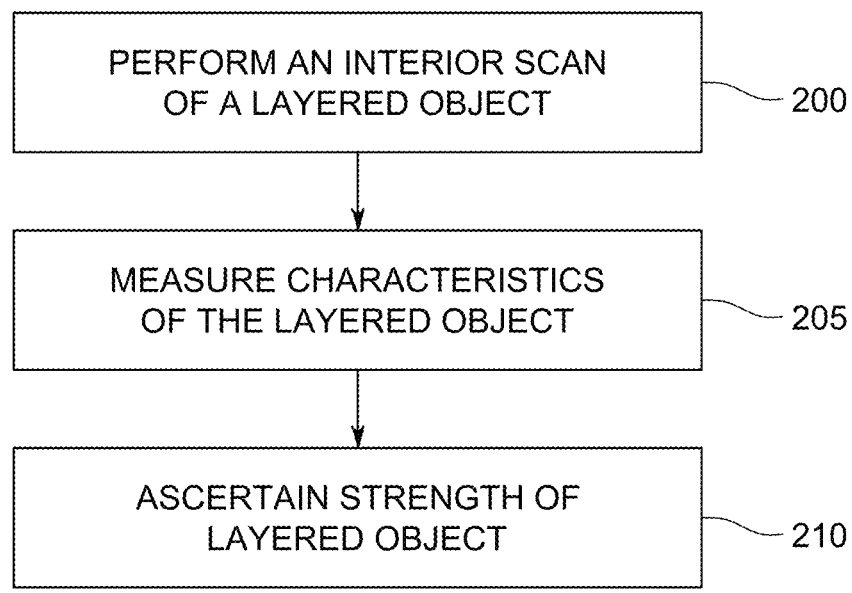
FIG. 8 is a process diagram illustrating a method of inspecting for defects within a turbine blade in accordance with one embodiment.

With reference to FIG. 8, a method of inspecting a layered object is described. At Step 200, a scan of an interior portion of a layered object is performed. The scan may be performed by any number of non-destructive imaging techniques capable of obtaining images of a plurality of planes throughout an object. Embodiments of the invention include ultrasound imaging, x-ray computed tomography imaging, and laminographic imaging.

Next, at Step 205, measurements are taken from the scanned images of various parameters located in the images. For example, if a defect is located in an image, the defect parameters of an external aspect ratio $L/a_e$, an internal aspect ratio $L_o/a_i$ the ratio of depth of the defect relative to the thickness of the layered object in the plane of the defect ($t_d/t_c$), and, the ratio of the height of the defect to the thickness of the layered object in the plane of the defect ($a_i/t_c$) can be taken. The equipment used may include an ultrasonic instrument capable of high resolution encoded scans. There are different techniques used for the acquisition of data, depending on the section of the blade to be inspected. This may require several chord-wise 122 and span-wise 124 scans that are then stitched together in an analytical software. There are several equipment vendors with supporting analytical software. Two such vendors include Olympus Corporation and Zetec, Inc.

Next, at Step 210, a strength profile of the layered object can be formulated by ascertaining the amount to which the layered object's strength has been compromised by the defect. This can be accomplished through the use of a look-up table, such as the look-up table 160.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. For example, while embodiments have been described in terms that may initially connote singularity, it should be appreciated that multiple components may be utilized. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. A method for inspecting a layered object, comprising:
   performing a scan of an interior portion of a layered object;
   measuring internal and external parameters of a defect within the layered object; and
   determining a strength of the layered object based on the measurements of one of the measured internal and external parameters of the defect,
   wherein the strength of the layered object is determined using a look-up table correlating structural strength of the layered object against at least one of the group consisting of an internal aspect ration of defect length to defect height, a ratio of depth of the defect relative to a thickness of the layered object in a plane of the defect, and a ratio of the defect height to a thickness of the layered object in a plane of the defect.

2. The method of claim 1, wherein said performing a scan comprises performing an ultrasound, a computed tomography, or a laminography scan.

3. The method of claim 1, wherein said performing a scan creates cross-sectional images of the interior portion of the layered object.

4. The method of claim 1, wherein the layered object comprises a wind turbine blade.

5. The method of claim 1, wherein the internal and external parameters is selected from the group consisting of an internal defect length, an external defect length, an internal defect height, an external defect height, a defect-to-surface thickness, a layered object thickness, or any combination thereof.

6. A method for inspecting a layered object, comprising:
   performing a scan of an interior portion of a layered object;
   measuring internal parameters of a defect within the layered object; and
   determining a strength of the layered object based on the measurements of one of the measured internal parameters of the defect,
   wherein the strength of the layered object is determined using a look-up table correlating structural strength of the layered object against at least one of the group consisting of an internal aspect ration of defect length to defect height, a ratio of depth of the defect relative to a thickness of the layered object in a plane of the defect, and a ratio of the defect height to a thickness of the layered object in a plane of the defect.

7. The method of claim 6, wherein said performing a scan comprises performing an ultrasound, a computed tomography, or a laminography scan.

8. The method of claim 6, wherein said performing a scan creates cross-sectional images of the interior portion of the layered object.

9. The method of claim 6, wherein the layered object comprises a wind turbine blade.

10. The method of claim 6, wherein the internal parameters is selected from the group consisting of an internal defect length, an external defect length, an internal defect height, an external defect height, a defect-to-surface thickness, a layered object thickness, or any combination thereof.

\* \* \* \* \*

UNITED STATES PATENT AND TRADEMARK OFFICE
CERTIFICATE OF CORRECTION

PATENT NO. : 8,418,560 B2  
APPLICATION NO. : 13/192747  
DATED : April 16, 2013  
INVENTOR(S) : Faidi et al.

Page 1 of 1

It is certified that error appears in the above-identified patent and that said Letters Patent is hereby corrected as shown below:

Title Page, Item (75), under "Inventors", in Column 1, Line 3, delete "TN" and insert -- TX --, therefor.

In the Specifications:

In Column 1, Line 45, delete "NexCore™" and insert -- NexCore™. --, therefor.

In Column 3, Line 27, delete "characteristics" and insert -- characteristics. --, therefor.

In Column 3, Line 33, delete "DESCRIPTION" and insert -- BRIEF DESCRIPTION --, therefor.

In Column 5, Line 59, delete "134," and insert -- $134_c$ --, therefor.

In Column 6, Line 3, delete "134," and insert -- $134_c$ --, therefor.

In Column 6, Line 58, delete "Lo/ai" and insert -- Lo/ai, --, therefor.

In the Claims:

In Column 7, Line 37, in Claim 1, delete "ration" and insert -- ratio --, therefor.

In Column 8, Line 23, in Claim 6, delete "ration" and insert -- ratio --, therefor.

Signed and Sealed this  
Second Day of July, 2013

Teresa Stanek Rea  
*Acting Director of the United States Patent and Trademark Office*